United States Patent [19]
Dijkema et al.

[11] Patent Number: 6,159,696
[45] Date of Patent: Dec. 12, 2000

[54] ISOLATED HUMAN BMP-4 PROMOTER REGION

[75] Inventors: Rein Dijkema, Oss; Arthur van den Wijngaard, Eindhoven, both of Netherlands

[73] Assignee: Akzo Nobel N.V., Arnham, Netherlands

[21] Appl. No.: 09/308,406

[22] PCT Filed: Nov. 20, 1997

[86] PCT No.: PCT/EP97/06668

§ 371 Date: Jun. 21, 1999

§ 102(e) Date: Jun. 21, 1999

[87] PCT Pub. No.: WO98/23740

PCT Pub. Date: Jun. 4, 1998

[30] Foreign Application Priority Data

Nov. 22, 1996 [EP] European Pat. Off. ............. 96203283

[51] Int. Cl.[7] .............................. C12Q 1/68; C07H 21/04; C12N 1/00; C12N 5/10; C12N 15/63
[52] U.S. Cl. ......................... 435/6; 435/243; 435/320.1; 435/325; 435/410; 536/24.1
[58] Field of Search ................ 536/24.1; 435/320.1, 435/325, 410, 243, 6

[56] References Cited

FOREIGN PATENT DOCUMENTS

| | | |
|---|---|---|
| 0 629 697 | 12/1994 | European Pat. Off. |
| 0 747 056 | 12/1996 | European Pat. Off. |
| WO 88 00205 | 1/1988 | WIPO |
| WO 95 33831 | 12/1995 | WIPO |
| WO 96 38590 | 12/1996 | WIPO |

OTHER PUBLICATIONS

Van den Wijngaaard, et al. "Genomic Organization of the Human Bone morphogenetic protein–4 gene: Molecular basis for multiple transcripts." Bioschemical and biophysical Research Communications. 219 (3) Feb. 27, 1996.

J. Feng et al., "The mouse bone morphogenetic protein–4 gene" Journal of Biological Chemistry vol. 2780, No. 47, Nov. 24, 2995 pp. 28364–28373.

T. Kurihara, et al., "Murine Bone morphogenetic promoters and exons for the 5'–untranslated region" Biochemical and Biophysical Research Communication, vol. 192, No. 3, 1993 pp. 1049–1056.

Davis V., et al. "Correlation between low levels of estrogen receptors and estrogen responsiveness in two rat osteoblast–like cell lines" Journal of bone and Mineral Research vol. 9, No. 7, Jul. 1994, pp. 983–991.

*Primary Examiner*—Terry McKelvey
*Attorney, Agent, or Firm*—Mary E. Gormley; William M. Blackstone

[57] ABSTRACT

The isolated human bone morphogenic protein-4 (BMP-4) promoter region, a vector comprising the isolated promoter region, and host cells comprising the isolated promoter region is described. A method for the identification of potential therapeutic agents for use in the prevention and/or treatment of osteoporosis, comprising the steps of: a) introducing into a cell a first expression vector comprising an isolated BMP-4 promoter region operably linked to a reporter gene, and a second expression vector comprising DNA encoding an estrogen receptor; b) contacting the cell with a candidate agent; and c) monitoring the expression of the protein encoded by the reporter gene, wherein induced expression of the protein indicates that the candidate compound is a potential therapeutic agent, is also described.

8 Claims, 11 Drawing Sheets

| EXON | (SIZE) | Exon 3' | intron (size) | Exon 5' |
|---|---|---|---|---|
| Exon 1 | (>262 bp) | CCTATGgtgagcaaggctacc.........intron 1 (1.9 kb)......... | | |
| Exon 2 | (>77 bp) | AACATGgtgggatttcctttc.........intron 2 (1.1 kb).........aaatattcctttagGAGCCA | | |
| Exon 3 | (125 bp) | CTGTCAgtcagtagacacctg.........intron 3 (1.2 kb).........cttccccctccccagAGACAC | | |
| Exon 4 | (377 bp) | ACGAAGgtcagtctcattaac.........intron 4 (1.0 kb).........cctaactgtgcctagAACATC | | |
| Exon 5 | (>987 bp) | | | |

FIG. 2

```
EcoRI
1166 GAATTCCGGATCTGGGCAAGTCCCTTTAACCTGGTAGTCCTTCCTTTCCTTGTTTGTAAAACAGAGAGATGAGGCTGATAGCTCCCTCACAGCTCCATCA

1066 GAGGCAGTGTGTGAAATTAGTCCTGTTTGGGAAGGTTAAAAGCCACCACATTCCACCTCCCTGCTAATATGATTACTAAAATGTTTTTATATGAAAGG

966 GCCAATTCCTCTCATCTCCCCTCTTCCTTTAAAAACAGACCAAGGGGCATCTTTTCTGTCTCCCCTGTGGCCTAAAAGGTTACTGCTTCTGTGGTTATCTCC

866 TTGGAAAGACAGAGTGTCAGGACTCTTAGGTACACCAAAAATGAACAACAAAAATCAACAACAACCATAACCAACAAAAATAACTGCTGTGTCGGTTCT
                                                                                           PstI

766 TAAGACGGCTTCTGAGCTAGAAACAGATTTTCTAACTGTAAAAAACGTGGCCCCAGCCTGTCTGCAGGCCACCTCTGTCTTTAGGCCTTGGGGGAGGA

666 GGGAAGTGAGCTCATTTACTGGGTCTACCTCAGGTCATCACCAAGGTGTTCTACAAAACGCACTTTAAGAATGTTTGGAAGGAAATTCACCTTTTAA

566 CAGCCCAAGAGGTATCTCTCTCTGGCACACAGCTTCTGCACAGTTTCTGCACAGTTTCGCACCTGTTTCTCAACGTTTGAAATCTTTTAACAGTTTATGGAAGGCCACCTTTTAAA
```

FIG. 5a-1

```
-  466  CCGATCCAACAGCTCCTTTCTCCATAACCTGATTTTAGAGGTGTTTCATTATCTCTAATTACTCAGGGTAAATGTGTGATTACTCAGTGTTTTAATCATCA
                                                                                   NcoI
                                                                                    |
-  366  GTTTGGGCAGCAGTTACACTAAACTCAGGGAAGCCCAGACTCCCCATGGGTATTTTGGAAGGTACGGCGACTAGTCGGTGCATGCTTTCTAGTACCTCCG

-  267  CACGTGGTCCCCAGGTGAGCCCAGCGCGTTCCCAGACTCCGAGGCAGCGGCAGCTGCGAGCTCCCGACGGCAGCTCGGGGCGCTGCCTGGGTATTC

-  167  CGGGACCCCGGGGCCTGCTAGGCGAGTCGGGCGGGAGGATGTGGGCGGGCTCCCCATCCCAGAAAGGAGGCGAGCGAGGGAGGAGGGAAGGAG
                                                                                  *
                                                                                 #*    *
-   66  GGAGGGGGCCGCCGGGGAAGAGAGGAGGAAGAGAGAAAGAGAGGAGGAAAGAGAGAAGAGCGAGGAGAGATGCGAGAAGGCAGAGAGGAGAGGAGGGA

+   35  GGGAAGGAGGCGGGAGCCCGGCTAGGTGAGTGTGGCATCCGAGCTGAGGGACGCGAGCCTGAGACGCCGCTGCTCCGCTGAGTATCTA
                                                       XhoI      EcoRV
                                                        |

+  135  GCTTGTCTCCCGATGGGATTCCCGTCCAAGCTATCTCGAGCCTGCAGCGCCACAGTCCCCGGCCCTGCCCAGGTTCACTGCAACCGTTCAGAGGTCCCC

+  235  AGGAGCTGCTGCTGGCGAGCCCGCTACTGCAGGGACCTATGgtgagcaaggctacc
```

```
      PstI
-1212 GGCTTCTTCCAGCGGGAGTTGGTCCGGGGGCCTTAGAGGCTCCAAGCACTGCTTTGGAGGATGCGGTTTGTGAGTTGAAGGCCTTT
-1112 GTGAGAGGTTAAACCCCCAAAAGATACATACTTGGTAAACTGAGGCTACCTGTAAACACATTCGGCATTAGGAGAAGATTCGAGTAGGAAGTGAAGGA
-1012 CAACCACCCGAGTTACATTCCTTCCCCCAATAAAAGCTCTGGGGATGAAAGTTCTTTTGGCTTTTATCTTTCGATTTAAAAATTTGAGAAGAAAAA
 -912 TGTGACTAGAGATGAATCCTGTGAATCCGAAATTGAAACACAACTCCCCCTTCCCCCTTCTACTGTCCCTTTGCCCCGCGGGCACAGCTTGCCTCCGTTTAGAACCGCGCTCTCCCGCCCCAGG
 -812 AGATTCCTTGGGGCCGAGGGTTTCCGGGGAACCCGGGCGCTCGCCCTTTGCCCCGCGGGCACAGCTTGCCTCCGTCCGTCTGCTTTCT
 -712 ACTTCTGGACCTCTCCCTGCCGGGCTTATTAAAGGGCTTCTGCGTCTCAAAACAAAAAAACCCTTTGCTCTTCCCAACCCTTTCGCAGCCCGCCC
```

- 612 CAGCGGTGGCGGGGACCAGCAAAGGCGAAAGCCGCGGGACGGTCGCGCGGAGGGCGCCCAGGGGCGCCTCCCGCCACCCGGACCTGAG

- 512 GTGTTGGTCGACTCCGGGCATCCACGGTCGGGAGGAGGCTGAGCTGTTCGATCCTTTACTTTTCTTCCTCAAAGTCTACCTGCCAATGCCCCTAACAA

- 412 CAAAACCAAGTATGTGCGTGAGAGTGGGGCGCAGGCAACCCGAGTTCTTGAGCTCCGGAGCGACCCAAAGCAGCAACTGGAACAGCCTCAGGAAAGG
                                                                      NciI

- 312 GAGGTCGGGTGGAGTGGGCTTTGGGGCAGGAGTCATGGGCCCGGACCTGGCCCTCCCGGCCCTGCTGAACGCTGAGTTGCGCCTAGTCGGG

- 212 TTTTCGAAGAGGCCCTGCCCAGAGACACCCAGACGATCTTCGATTAGTCAGGACATCCCAGTAACTGCTTGAACTGTAGGTAGGTAAAATT

- 112 CTTGAAGGAGTATTGCTGCGTGCCGACTCTGCTGCTGTGCAACGAGGAAGGGGTGGGGAAGGAAGTGGCGGGAAGAGTGTGGTGGTGGTTTAAA
         *  *  *
         #                                                               NciI

- 12 AAATAAGGGAAGCCGAGGCGAGAGAGACGCAGAGGTCGAGCGCAGGCCGAAAGCTGTTCACCGTTTTCTCGACTCCGGGAACATGgtgggattt
                                                                       PstI    EX2REVA + 89 cctttctgcgcgggtcggagttgtaaaacctcggccacattaagatctgaaaactgtgatgcgtccttttctgcag

FIG. 5b-2

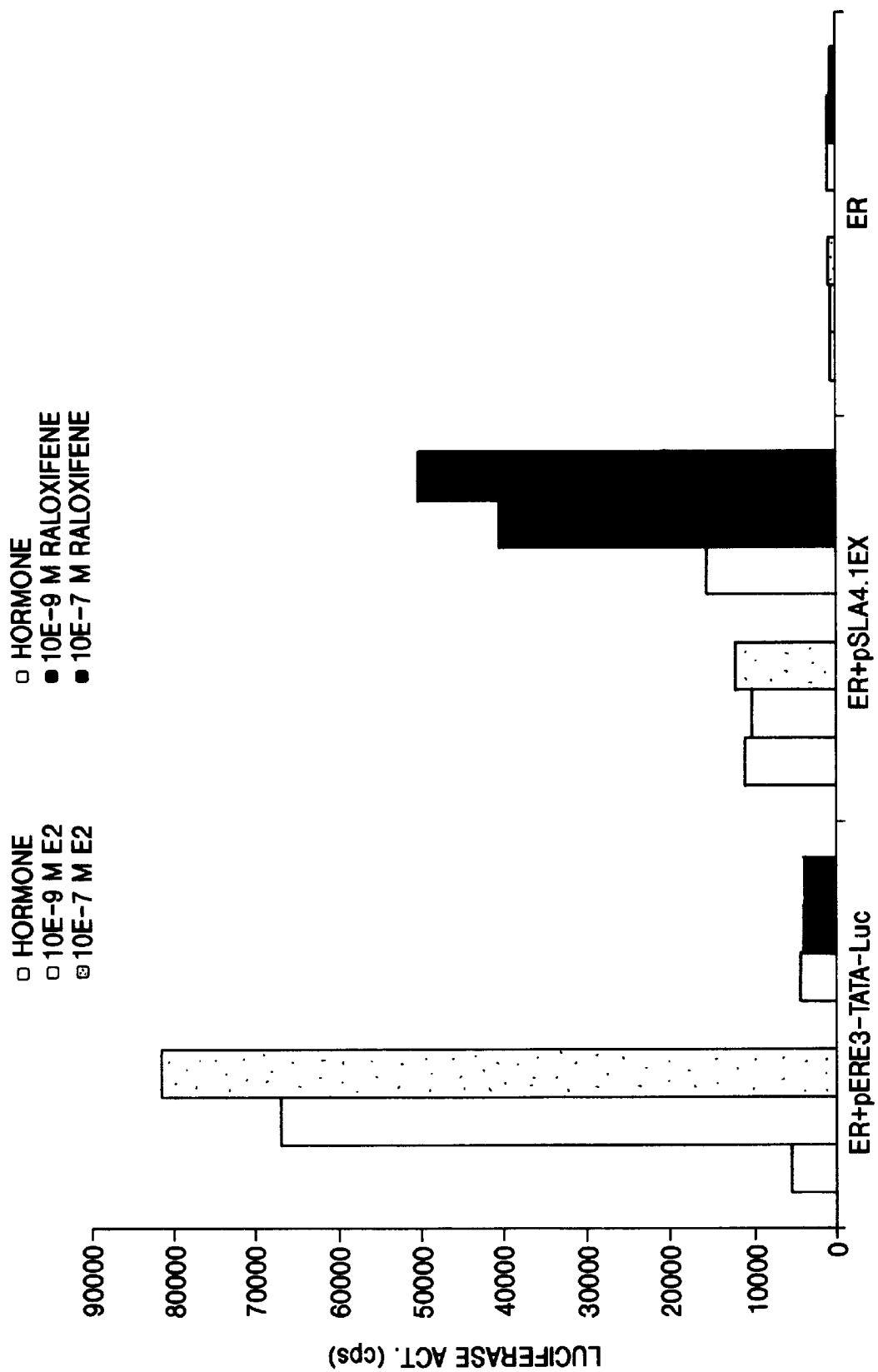

ISOLATED HUMAN BMP-4 PROMOTER REGION

CROSS-REFERENCES TO RELATED APPLICATIONS

This application is a 371 of PCT/EP97/06668, filed Nov. 20, 1997.

FIELD OF THE INVENTION

The present invention relates to a method for the screening of therapeutic agents for the prevention and/or treatment of osteoporosis. The present invention relates to the isolation and cloning of the promoter regions of the gene encoding the mammalian bone morphogenetic protein-4 and the use of said promoter regions for the construction of recombinant expression vectors. The present invention further relates to cells which comprise recombinant expression vectors in which said promoter regions are operably linked to a reporter gene. Furthermore, the present invention relates to a method for the identification of therapeutic agents for the prevention and/or treatment of osteoporosis.

BACKGROUND OF THE INVENTION

Osteoporosis is a bone disorder characterized by the loss of bone mass, which leads to fragility and porosity of the bone of man. As a result patients suffering from osteoporosis have an increased fracture risk of the bones. Especially in postmenopausal women osteoporosis is one of the major syndromes, resulting from the reduction of estrogen production by the ovaries. In general, the loss of bone in postmenopausal women is prevented or treated by estrogen replacement: when administered at low levels, the estrogens have a beneficial effect on the loss of bone. However disadvantages of the so called estrogen replacement therapy are the unwanted side effects of estrogens on the endometrium, i.e. the increased risk of breast carcinomas and endometrium stimulation and/or hyperplasia, resulting in the increased risk of endometrium carcinomas.

In the light of these serious side effects there is a strong need for an alternative treatment of osteoporosis, in which the use of estrogens is avoided. It is an object of the invention to provide for such alternative and safer routes for the prevention and/or treatment of osteoporosis.

The bone morphogenetic proteins (BMPs) are a group of proteins that can induce de novo cartilage and bone formation, and appear to be essential for skeletal development during mammalian embryogenesis (Wang, *Trends Biotechnol.* 11, 379, 1993). Due to their osteoinductive properties the BMPs can be of clinical interest. Recently, it has become evident that early in the process of fracture healing the concentration of bone morphogenetic protein-4 (BMP-4) increases dramatically (Nakase et al., *J. Bone Miner. Res.* 9, 651, 1994 and Bostrom et al., *J. Orthopaed. Res.* 13, 357, 1995). In vivo experiments show that upregulation of BMP-4 transcription indeed promotes bone healing in mammals (Fang et al., *Proc. Natl. Acad. Sci. USA.* 93, 5753, 1966). These observations suggest an important role of BMP-4 in bone remodeling and fracture repair.

Although the role of BMP-4 seems to be crucial during many stages of development, the regulatory mechanisms underlying the specific expression of the BMP-4 gene are unknown. BMP-4 transcripts are expressed in several specific tissues, shown by Northern blot analysis and in situ hybridization. Two human BMP-4 transcripts have been identified, which are completely identical in their coding region, but are different in their 5' non-coding regions. Previous investigations showed a cell line dependent expression of both transcripts. Interestingly, the presence of multiple transcripts suggested an important difference in BMP-4 gene regulation. Furthermore, the short half life of BMP-4 mRNA suggests that the gene is primarily regulated at transcriptional level (Rogers et al., *Cell. Growth. Differ.* 7, 115, 1996).

SUMMARY OF THE INVENTION

According to the present invention it was found that the regulation of BMP-4 results in an alternative therapeutic route for fracture repair and the prevention or treatment of osteoporosis. Since the local production of BMP-4 seems to be more efficient in inducing bone formation than exogenous delivery of recombinant protein, the treatment according to the present invention is based on the modulation of the tissue-specific, local expression of BMP-4 in the osteoblasts. It was suprisingly found that the expression of the BMP-4 gene could be induced and/or stimulated by tamoxifen and raloxifene. These well known anti-osteoporosis agents prevent loss of bone, and as such preserve the bone density, while having diminished or no effects on the uterus or breast. Furthermore, it has been established both in vitro as well as in vivo that these compounds antagonize the action of 17β-estradiol in ER-mediated gene transcription modulation on the level of the uterus or breast cell. It has now been established for the first time that these anti-osteoporosis agents exert their beneficial activities via ER-mediated regulation of the expression of the BMP-4 gene. According to the present invention the ER bound to certain compounds (thus forming a compound/ER complex) regulate the expression of the BMP-4 gene. Estrogens such as 17-β-estradiol, however did not show a significant transcriptional effect on the expression of the BMP-4 gene, indicating that estrogens exert their anti-osteoporotic activity via a mechanism different from the mechanism via which tamoxifen and raloxifene display their anti-osteoporotic activity. Hence, the identification of factors that regulate the BMP-4 gene on a transcriptional level, in a bone tissue specific manner leads to the identification of therapeutic agents which control fracture repair and prevent bone loss.

It is an object of the invention to provide a method for the identification of therapeutic agents that modulate the ER-mediated expression of the BMP-4 gene, said modulation resulting in a beneficial effect in the prevention or treatment of osteoporosis, whereby said therapeutic agents do not display the unwanted side effects on breast or uterus. It is also an object of the invention to provide materials which can be used in this method according to the invention.

DETAILED DESCRIPTION OF THE INVENTION

In one aspect the present invention provides for the human BMP-4 promoter regions, and fragments of said promoter regions. By "promoter regions" is understood the nucleic acid sequence of the region upstream of the encoding sequences of the human BMP-4 gene, whereby said nucleic acid sequences modulate and control the expression of the human BMP-4 gene. Preferably, the BMP-4 promoter region is the promoter 1 (P1) region or the promoter 2 (P2) region. More preferably the BMP-4 promoter regions according to the invention have the nucleic acid sequence shown in SEQ ID NO:1 or SEQ ID NO:2 or fragments thereof, provided that said fragments modulate and/or control the expression of the downstream encoding sequences of a gene. Promoter region fragments according to the invention are, for example, nucleotide fragment −1166 to +173, nucleotide fragment −697 to +173, nucleotide fragment −323 to +173 nucleotide fragment −323 to +33, nucleotide fragment −323 to +16, and nucleotide fragment −323 to −42 of the nucleotide sequence of promoter region 1 as depicted in FIG. 5a or nucleotide fragment −1212 to +70, nucleotide fragment −247 to +70 of the nucleotide sequence of promoter 2 region as depicted in FIG. 5b.

In another aspect the invention provides for recombinant expression vectors which comprise a human BMP-4 promoter region operably linked to a gene, preferably a reporter gene. Preferably the vector according to the invention comprises the promoter 1 (P1) region or promoter 2 (P2) region. More preferably the vector according to the invention comprises a promoter region having the nucleic acid sequence shown in SEQ ID NO:1 or SEQ ID NO:2, or fragments thereof.

Suitable expression vectors according to the invention are, for example, bacterial or yeast plasmids, wide host range plasmids and vectors derived from combinations of plasmid and phage or virus DNA. Vectors derived from chromosomal DNA are also included. Furthermore an origin of replication and/or a dominant selection marker can be present in the vector according to the invention. The vectors according to the invention are suitable for transforming a host cell.

Suitable host cells according to the invention are bacterial host cells, yeast and other fungi, plant or animal host such as Chinese Hamster Ovary cells or monkey cells. Thus, a host cell which comprises the DNA or expression vector according to the invention is also within the scope of the invention.

Suitable reporter genes that can be used for constructing an expression vector according to the invention are for example the bacterial chloramphenicol acetyl transferase (CAT) gene, the firefly luciferase gene, and the β-galactosidase gene.

Preferred vectors according to the invention are pSLA4.1EX, pSLA4.1PX, pSLA4.1NX, pSLA4.1N+33, pSLA4.1N+16, pSLA4.1N−42, pSLA4.2PN, and pSLA4.2NN.

The techniques for the preparation of the DNA or the vector according to the invention as well as the transformation or transfection of a host cell with said DNA or vector are standard and well known in the art, see for instance Sambrook et al., *Molecular Cloning: A laboratory Manual.* 2$^{nd}$ Ed., Cold Spring Harbor Laboratory, Cold Spring Harbor, N.Y., 1989.

The BMP-4 promoter regions and expression vectors according to the invention can be used for the in vitro identification of compounds that modulate the expression of the BMP-4 gene and such compounds are potential therapeutic agents for use in prevention or treatment of osteoporosis. Thus, in a further aspect the invention provides for a method for the identification of therapeutic agents for use in the prevention or treatment of osteoporosis, said method comprising the steps of:

a) introducing into a host cell a first expression vector comprising a BMP-4 promoter region operably linked to a reporter gene, and a second expression vector comprising DNA encoding the estrogen receptor and capable of expressing said estrogen receptor;

b) contacting said cell with compounds having possible therapeutic activity; and c) monitoring the expression of the protein encoded by the reported gene.

Preferably the host cell is mammalian, more preferably of human origin. Most preferred are host cells derived from human osteoblast lineage. Preferably the first expression vector comprises promoter 1 region or promoter 2 region, more preferably the nucleic acid sequence depicted in SEQ ID NO:1 or SEQ ID NO:2 or fragments thereof, provided that said fragments modulate and/or control the expression of said reporter gene.

If the compound tested shows affinity for the estrogen receptor (ER) it will bind to the ER expressed by the second expression vector. If the resulting compound/ER complex binds to the BMP-4 promoter region and induces the expression of the reporter gene under control of said BMP-4 promoter region, the presence of the reporter protein indicates the potential of said compound to activate the BMP-4 promoter and in that way regulate the expression of the BMP-4 gene. 17β-estradiol tested in the method according to the invention did not induce the expression of the reporter gene, indicating that the 17β-estradiol/ER complex does not activate the BMP-4 promoter. It was found that tamoxifen and raloxifene, when tested in the method according to the invention, induced expression of the reporter gene. On the other hand, neither of these compounds were able to induce expression of the reporter gene, when the reporter gene was under the control of a promoter comprising an estrogen responsive element (ERE).

The present invention thus provides for a quick and economic method to screen for therapeutic agents for the prevention and/or treatment of osteoporosis. The method according to the invention furthermore provides for the selection of therapeutic agents that on one hand have a beneficial effect the bone, but diminished or no side effects on breast or uterus. The method according to the invention is especially suited to be used for the high throughout screening of numerous potential compounds.

Thus, according to a further aspect of the invention, compounds that are identified in the method according to the present invention can be used for the preparation of a pharmaceutical composition for the stimulation of BMP-4 production. More specifically, the compounds identified with the method according to the invention can be used for the preparation of a pharmaceutical composition for the prevention and/or treatment of bone loss. More particularly, the compounds identified with the method according to the invention can be used for the preparation of a pharmaceutical composition for the prevention and/or treatment of osteoporosis.

It was suprisingly found that ICI 164384 modulates the ER-mediated expression of BMP-4. ICI 164384 is well known as a anti-tumor agent. However, when the compound was tested in the method according to the invention, it resulted in a considerable expression of the reporter gene. Hence it could be concluded that, in vivo, ICI 164384 modulates the expression of BMP-4 gene an as such stimulates bone formation. This makes ICI 164384 suitable for use in anti-osteoporosis therapy.

Hence the present invention provides for the use of ICI 164384 in the manufacture of a medicament for the prevention and/or treatment of osteoporosis.

BRIEF DESCRIPTION OF THE DRAWINGS

FIG. 2 Exon-intron boundaries of the BMP-4 gene. Nucleotide sequence for each intron/exon boundary and size of each exon and intron are shown. The 5' site of exon 1 and 2 is not shown in this figure, for more information see FIG. 5. The 3' site of exon 5 is not shown because of its unknown poly(A+) addition site. The 3' splice site of exon 1 is shown in SEQ ID NO: 10; the 3' splice site of exon 2 is shown in SEQ ID NO: 11 and the 5' splice site of exon 2 is shown in SEQ ID NO: 12. The 3' splice site of exon 3 is shown in SEQ ID NO: 13, and 5' splice site of exon 3 is shown in SEQ ID NO: 14. The 3' splice site of exon 4 is shown in SEQ ID NO: 15 and the 5' splice site of exon 4 is shown in SEQ ID NO:16.

FIGS. 5a–5b Nucleic acid sequence of BMP-4 promoter 1 region (FIG. 5a; SEQ ID NO:1) and BMP-4 promoter 2 region (FIG. 5b; SEQ ID NO:2). Bases are numbered relative to the transcription start site (+1) that was found initially; a second transcription start site was later found at −69. Transcription start sites found by primer extension (#) and by RACE-PCR (*) are indicated. Introns are in normal letters. Positions of primer EX1REVA and EX2REVA, used in primer extension, are underlined.

FIG. 6 Histogram showing the differential ER-mediated effects of 17β-estradiol and raloxifene on reporter constructs, that were based on either an estrogen response element-containing promoter (pERE$_3$TATA-Luc) or the promoter 1 region derived from BMP-4 (pSLA4.1EX) in front of the firefly luciferase gene. The individual reporter constructs, together with an expression plasmid for the human estrogen receptor (pKCRE-ER), were transiently transfected in the osteosarcoma cell line U-2 OS.

EXAMPLES

Cell Culture

Several human cell lines were used, including the embryonal carcinoma cell line Tera-2 (Mosselman et al., Cancer Res. 54, 220, 1994) and the osteosarcoma cell line U-2 OS (ATCC HTB 96). A 1:1 mixture of Dulbecco's modified medium (DMEM) and Ham's F12 medium supplemented with 10% (v/v) fetal calf serum (FCS) was used for culturing U-2 OS; MEM and 10% FCS was used for Tera-2 in the presence of 7.5% $CO_2$-atmosphere at 37° C.

Isolation of the Human BMP-4 Gene

A 1.3 kb mouse full length BMP-4 cDNA fragment (mmBMP4) was obtained by PCR on a lambda gt10 8½ day C57BL mouse cDNA library (gift from Dr. B. L. M. Hogan, Vanderbilt University, Nashville, Tenn.), using primers F4

(5'-CGCGGATCCCAAGTTTGTTCAAGATTGGCT-3'; SEQ ID NO:3)

and R4

(5'-CGCGGATCCGCCTGATCTCAGCGGCACCC-3'; SEQ ID NO:4)

based on human BMP-4 cDNA sequence HSBMP2B (Gen EMBL, gcg accession number M22490). This probe was used to screen a human genomic cosmid library (Ouweland et al., *Biochim. Biophys. Acta* 825, 140, 1985; gift from Mr. J. van Groningen, University of Nijmegen, The Netherlands). Approximately $3 \times 10^5$ cosmid clones were screened under non-stringent conditions in 5× SSC, 5× Denhardt's, 0.5% SDS, 100 µg/ml denatured herring sperm DNA at 65° C. overnight with the $^{32}$P-labeled mmBMP4 probe, and filters were washed up to 0.1× SSC/ 0.1% SDS at 65 ° C. prior to autoradiography. One of the positive cosmid clones with a 38 kb insert was further purified and analyzed.

Genomic Clone Mapping and DNA Sequencing Analysis

Figure 1:
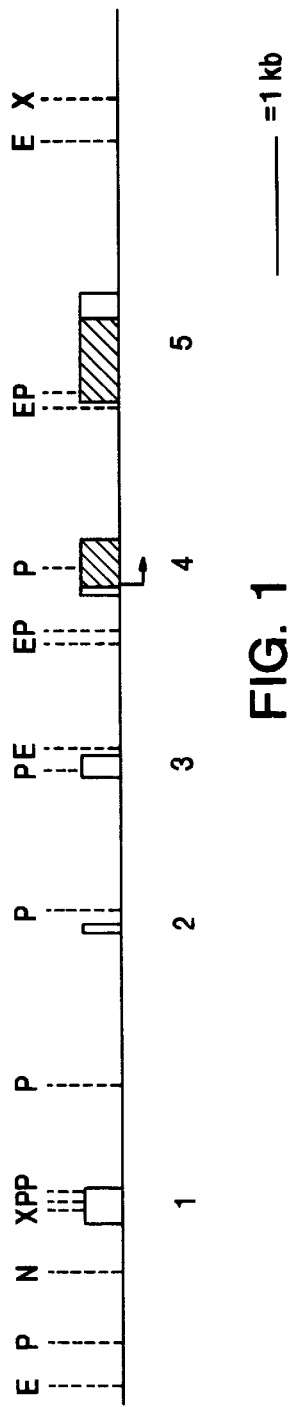
FIG. 1 Structure and restriction map of the human BMP-4 gene. Only a part of the gene containing the five exons are shown. Exons (solid bars) are indicated by the numbers 1 to 5. The coding region (shaded box) is shown together with the location of the proposed translation start site within exon 4 (arrow). Only restriction sites relevant for the physical map are indicated: E, EcoRI; X, XhoI; P, PstI and N, NcoI.

Cosmid DNA was purified and submitted to Southern blot analysis after digesting with appropriate endoR's to generate a physical map. The DNA was transferred onto Hybond-N membrane (Amersham) and probed with the mmBMP4 fragment or BMP-4-specific primers (F4 and R4) to determine the orientation of the gene and approximate position of exons (FIG. 1). Fragments that hybridized with these probes were subcloned into pbluescript II KS(−) (Stratagene) and analysed by DNA sequence analysis using the T7-Sequencing Kit (Pharmacia). In addition, for identification of the splice junctions of the BMP-4 gene, internal primers were chosen near possible splice junctions. These primers were used for direct cosmid DNA sequencing, according to the dsDNA Cycle Sequencing System (GibcoBRL). The obtained genomic sequences were compared with the mouse BMP-4 gene (Gen EMBL, gcg accession number X56840) and several human BMP-4 cDNA sequences using computer analysis (Fasta, Caos Cammsa, NL), showing that the 38 kb genomic clone contained the entire BMP-4 gene. The exact localization and sequence of splice sites is shown in FIG. 2. All of the exon/intron boundaries defining the splice sites are conform the consensus sequence of AG at the 3'-acceptor splice site and GT at the 5'-donor splice site.

Rapid Amplification of the 5'-cDNA Ends of the Human BMP-4 Transcripts

Figure 3:
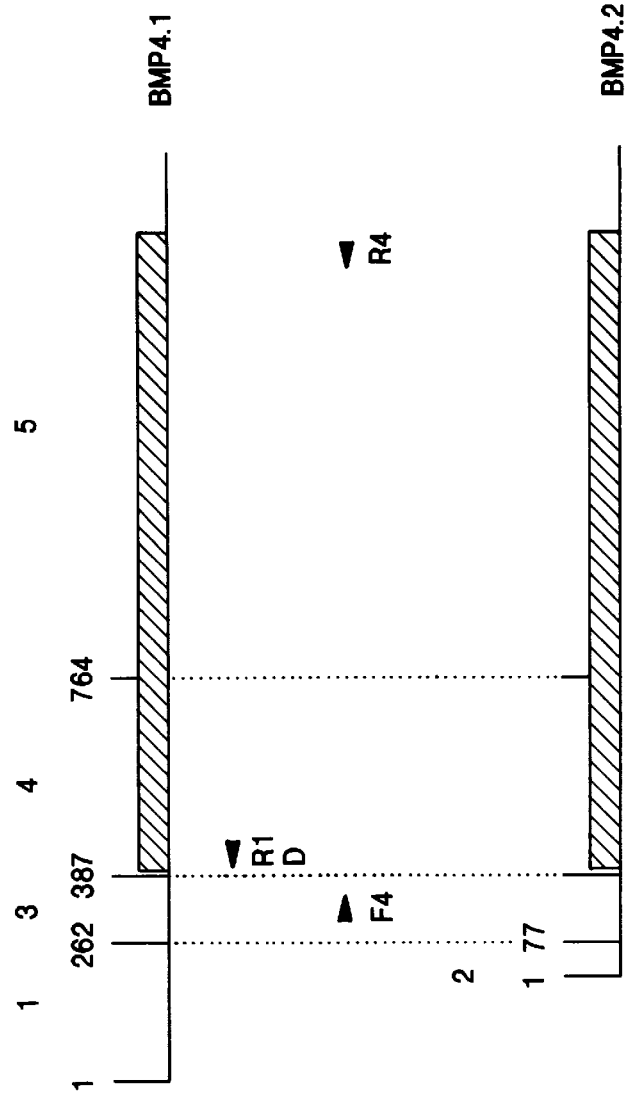
FIG. 3 Location of primers for the two BMP-4 transcripts. The location of introns (vertical lines), together with the first nucleotide position of each exon (numbers), are indicated. The coding region (shaded box) and exons (bold numbers) are shown. The first BMP-4 transcript (BMP4.1), is the same as HSBMP2B (Gen EMBL, gcg accession number M22490), which contains exon 1, 3, 4 and 5. From the second transcript (BMP4.2) only the length of exon 2 is indicated (Chen et al., *Biochim. Biophys. Acta* 1174, 286, 1993), which is spliced to exon 3, 4 and 5 at nucleotide position 262 of the HSBMP2B sequence (Gen EMBL, gcg accession number M22490). The sequence of exon 3, 4 and 5 of both transcripts is exactly the same. Primers (arrow heads) are shown as reverse (R) and forward (F).

The 5'-AmpliFinder Race kit (Clontech) was used to isolate cDNA containing full length 5'-ends of the human BMP-4 transcripts. The first cDNA strand was synthesized according to the supplier's specification, using oligo dT$_{12-18}$ (Gibco) and 2 µg poly A+ from Tera-2 cells. A specially designed single-stranded anchor oligonucleotide (provided with the kit) was ligated to the 3'-end of cDNA using T4 DNA ligase. Following anchor ligation, a portion of the cDNA was amplified by PCR, using a primer complementary to the anchor and a primer within exon 4 (R1D; 5'-GCATTCGGTTACCAGGAATCATGG-3'; SEQ ID NO:5). PCR products were subcloned into plasmid pGEM-T (Promega) and sequenced using the T7-Sequencing Kit (Pharmacia). Sequence analysis revealed that one transcript was identical to a previously described cDNA from an osteosarcoma cell line (Gen EMBL, gcg accession number M22490) and that the other transcript was identical to a cDNA from a prostate cancer cell line (Chen et al., *Biochim. Biophys. Acta* 1174, 286, 1993). In addition, comparison of both transcripts with the genomic structure indicated that one transcript contains exon 1, 3, 4 and 5 (named BMP4.1) and that the other contains exon 2, 3, 4 and 5 (named BMP4.2). Both transcripts, location of primers and the nucleotide position of the introns are shown in FIG. 3.

Sequencing of the 5'-Flanking Region of Promoter 1 and Promoter 2

Figure 4:
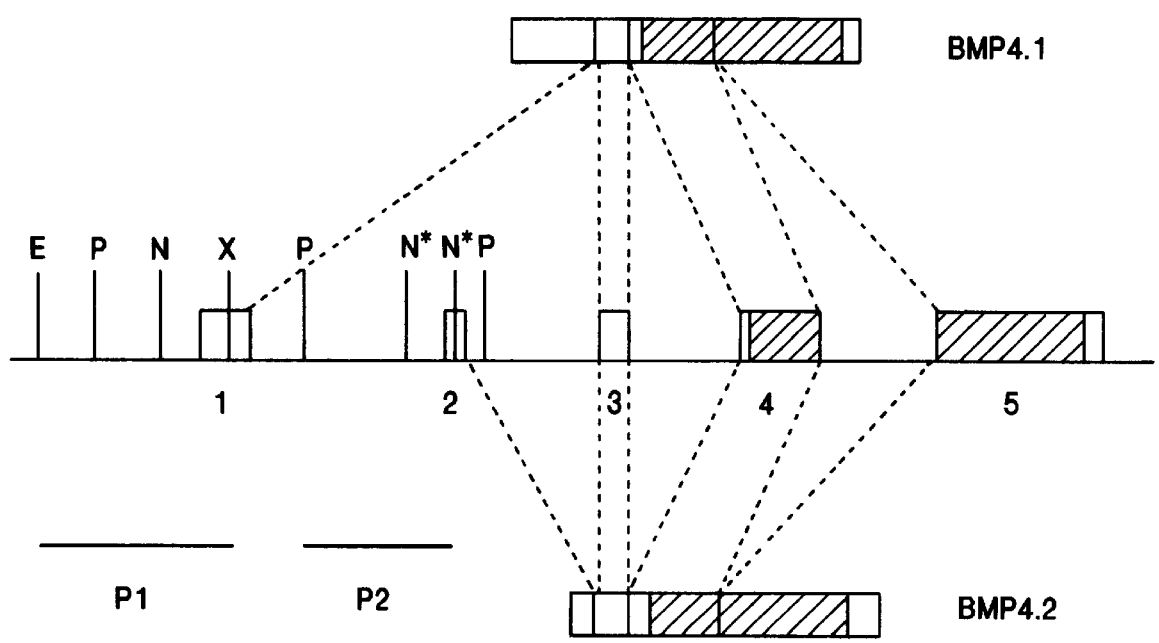
FIG. 4 Schematic representation of the human BMP-4 gene. Exons (solid bars) are indicated by the numbers 1 to 5. The coding region (shaded box) is shown within the exons as well as both exon 1 and exon 2 derived transcripts (BMP4.1 and BMP4.2, respectively). Only restriction sites relevant for cloning promoter fragments are indicated: E, EcoRI; X, XhoI; P, PstI, N, NcoI and N*, NciI. The location of the two promoter regions (P1 and P2) is represented by a bold line.

The human BMP-4 gene consists of 5 exons, of which the first three exons are non-coding (exon 1, 2 and 3), while exon 4 and 5 encode the BMP-4 protein. BMP4.1 (exon-1-3-4-5) and BMP4.2 (exon-2-3-4-5) result from two putative promoter regions, which were designated P1 and P2. A partial restriction map and the two putative promoter regions are schematic representated in FIG. 4. We have cloned and sequenced promoter P1 and P2, in order to functionally characterize both regions. An 1.3 kb endoR EcoRI/XhoI promoter 1 fragment, encompassing the up-stream promoter and part of the exon 1 coding region, and a 1.3 kb endoR PstI promoter 2 fragment, encompassing the up-stream promoter and the full exon 2 coding region, were obtained by genomic BMP-4 cosmid DNA digestion. To obtain the whole sequence, parts of the promoter fragments were subcloned in pBluescript and sequenced in both directions using the T7-Sequencing Kit (Pharmacia). Direct cosmid sequencing (as described above) was used to sequence the 3'-site of exon 1 and a part of the intron. The sequence of both promoter regions are shown in FIG. 5.

Transcription Start Sites

Both promoters are TATA-less, but contain several consensus sequences which are supposed to be involved during transcription initiation, like the GC-rich sequence. In order to determine the location(s) at which the transcription initiates within the BMP-4 gene, we analyzed this region via a primer extension and RACE-PCR amplification.

Using rapid amplification of cDNA ends (RACE-PCR), the 5'-ends of the human BMP-4 mRNAs were cloned and characterized. The BMP-4 mRNA found in RACE-PCR (as described above), ended at various points in the 5'-portion of exon 1 or exon 2, as indicated in FIG. 5. The finding that the 5'-UTR of both mRNAs are identical with exon 1 or exon 2, indicated that both BMP-4 transcripts are indeed transcribed from the two cloned promoter regions.

Primer extension analysis was performed according to the primer extension system (Promega) using oligonucleotides as primers. The primers used in this experiment correspond to the antisense sequence within exon 1 or exon 2 of the BMP-4 gene; respectively EX1REVA (5'-CAGCTCGGATGCCACACTCAC-3'; SEQ ID NO:6) and EX2REVA (5'-CATGTTCCCGGAGTCGAG-3'; SEQ ID NO:7), see FIG. 5 for detail. Each primer was end-labeled with T4 polynucleotide kinase and [$\gamma$-$^{32}$p] ATP, and approximately $5 \times 10^5$ cpm of primer was mixed with 500 ng U-2 OS poly A+ RNA, 250 ng Tera-2 poly A+ or 10 µg yeast tRNA. The primer/RNA mixture was denatured at 95° C., and incubated for 1 hr at 55° C. to anneal the primer. Primer extension was completed for 1 hour at 50° C. using Superscript II (Gibco) as reverse transcriptase. The size of the primer extension products was analyzed on a sequence gel, by comparison with a known DNA sequence.

Initially, the most prominent primer extension product was found to coincide with the position determined by RACE-PCR or the most 5'-UTR of published BMP-4 cDNAs. The results presented here show that both promoters have multiple transcription start sites, but at clustered positions, in a GC-rich region. The most upstream start site is arbitrarily assigned to +1 position (FIG. 5). Using a different EX1REVA primer, a more upstream transcription site in promoter region 1 was identified and found to be at position −69 (FIG. 5a).

BMP-4 Promoter Constructs

BMP-4 promoter region constructs were generated by standard cloning procedures (Sambrook et al., *Molecular Cloning: A Laboratory Manual.* 2$^{nd}$ Ed., Cold Spring Harbor Laboratory, Cold Spring Harbor, N.Y., 1989). Promoter region fragments were blunt-ended with klenow and deoxynucleotidetriphosphates, and subcloned into an endoR SmaI-digested pSLA4 luciferase reporter plasmid (Afink et al., *Oncogene* 10, 1667, 1995). The construct pSLA4.1EX contains the 1.3 kb endoR EcoRI/XhoI promoter 1 fragment (−1166/+173); construct pSLA4.1PX the 0.9 kb endoR PstI/XhoI promoter 1 fragment (−697/+173), and construct pSLA4.1NX contains the 0.5 kb endoR NcoI/XhoI promoter 1 fragment (−323/+173) (FIG. 5a). The construct pSLA4.2PN contains the 1.3 kb endoR PstI/NciI promoter 2 fragment (−1212/+70) and construct pSLA4.2NN contains the 0.3 kb endoR NciI/NciI promoter 2 fragment (−247/+70) (FIG. 5b). Additional fragments of promoter region 1 were generated by progressive exonuclease III digestion (Erase-a-base Kit, Promega), blunt-ended with klenow and deoxynucleotide-triphosphates and subcloned into an endoR SmaI-digested pSLA4 luciferase reporter plasmid. In this way constructs were obtained like pSLA4.1N+33 containing the nucleotide fragment−323/+33, pSLA4.1N+16 containing nucleotide fragment−323/+16 and pSLA4.1N−42 containing nucleotide fragment−323/−42 (FIG. 5a).

Plasmids were purified using Qiagen tip-100 columns according to the manufacturer's instructions. Sense orientation of all inserts with respect to the pSLA4 vector was verified by DNA sequencing.

ERE Promoter Construct

The estrogen response element (ERE)-containing promoter construct was based on pBL-CAT6 (Boshart et al., Gene 110, 129, 1992). It was modified into a luciferase (Luc) reporter construct by exchanging the endoR XhoI/StyI fragment of pBL CAT6 (containing the chloramphenicol acetyl transferase coding information) by the endoR XhoI/StyI fragment of pXP2 (containing the luciferase coding information; Nordeen et al., *Biotechniques* 6, 454, 1988). A minimal promoter/TATA-element with the sequence 5'-GGGTATATAAT-3' (SEQ ID NO:8) was inserted in between the endoR XbaI and endoR BamHI sites resulting in plasmid pTATA-Luc. A triple estrogen response element (ERE) with the core sequence

5'-AGGTCACAGTGACCT-3' (SEQ ID NO:9)

was inserted in the endoR HindIII site resulting in plasmid pERE$_3$TATA-Luc.

Human ER Expression Construct

The human estrogen receptor (ER)-containing mammalian expression construct pKCRE-ER was constructed in the following way. The human ER-cDNA was obtained from G.

Greene (Ben May Laboratory for Cancer Research, University of Chicago); it encodes a glycine instead of valine at amino acid position 400 (G. Greene et al., *Science* 231, 1150, 1986 and Tora et al., *EMBO. J*, 8, 1981, 1989). The ER-cDNA was isolated as an endoR SphI/EcoRI fragment comprising nucleotide positions −30 to +1800. This fragment was blunted by T4-DNA polymerase and inserted in the blunted endoR BamHI site of the mammalian expression construct pKCR (O'Hara et al., *Proc.Natl.Acad.Sci.USA*, 78, 1527, 1981). The latter plasmid was modified in that the last exon region of the rabbit β-globin gene was removed by digestion with endoR EcoRI/BglII, filling in, and religation (nucleotide position 1122–1196; Van Ooyen et al., *Science* 206, 337, 1979) and the replacement of pBR322 for pBR327 sequences.

Test Compounds

Apart from 17β-estradiol, a number of estrogen analogs were used, that comprise raloxifene, 4OH-tamoxifen and ICI 164.384. Their chemical structures have all been described (Evans et al., *Bone* 17, 183S, 1995).

Transient Transfections

ER-mediated reporter gene modulation by different estrogen analogs of individual promoter region constructs were assayed by transient transfection of osteosarcoma cells (U-2 OS). One day prior to transfection, U-2 OS cells were seeded at a density of $10^5$ cells per well (6-well tissue culture plates; Nunc). In this case, the cells were seeded in fenolred-free medium containing 10% (v/v) charcoal-stripped Fetal Calf Serum (csFCS) instead of FCS. DNA was introduced using the lipofection method as described by the supplier (Gibco, BRL). Hereto, the DNA (1 μg receptor construct, 1 μg reporter construct and 250 ng transfection control construct in 250 μL Optimem, Gibco BRL; in different experiments the total amount of transfected DNA was kept constant using pKCRE) was mixed with an equal volume of Lipofectin Reagent (Gibco, BRL) and allowed to stand for 30 min at room temperature. To this was added 500 μL of Optimem (RT) and this mixture was added to the cells, after the latter have been washed with serum-free medium. After a 5 h incubation period at 37° C., the cells were washed with fenolred-free and serum-free medium and incubated overnight in fenolred-free and 10% csFCS medium containing the testcompounds at the concentrations indicated. Prior to the preparation of lysates, cells were washed with PBS (7.6 mM $Na_2HPO_4$/$NAH_2PO4$ pH 7.4 and 0.12 M NaCl). Cell extracts were prepared by the addition of 200 μL lysis buffer (0.1 M sodium phosphate buffer pH 7.8 and 0.2% Triton X-100) to the cells and allowed to stand for 5 min at room temperature. Luciferase measurements of cell extracts was performed as described by the supplier (Promega; Luciferase assay system E1501). Hereto, 30 μL of cell extract was added to a 60-well Optiplate (Packard) and combined with 50 μL of luciferase substrate. The plates were sealed with Topseal film (Packard) and measurements were performed in a Topcount (Packard).

In this way, FIG. 6 is demonstrating the differential ER-mediated effects of 17β-estradiol (E2) and raloxifene towards two reporter constructs being based on an estrogen response element promoter in pERE₃TATA-Luc and a BMP-4 promoter in pSLA4.1EX.

Figure 7:
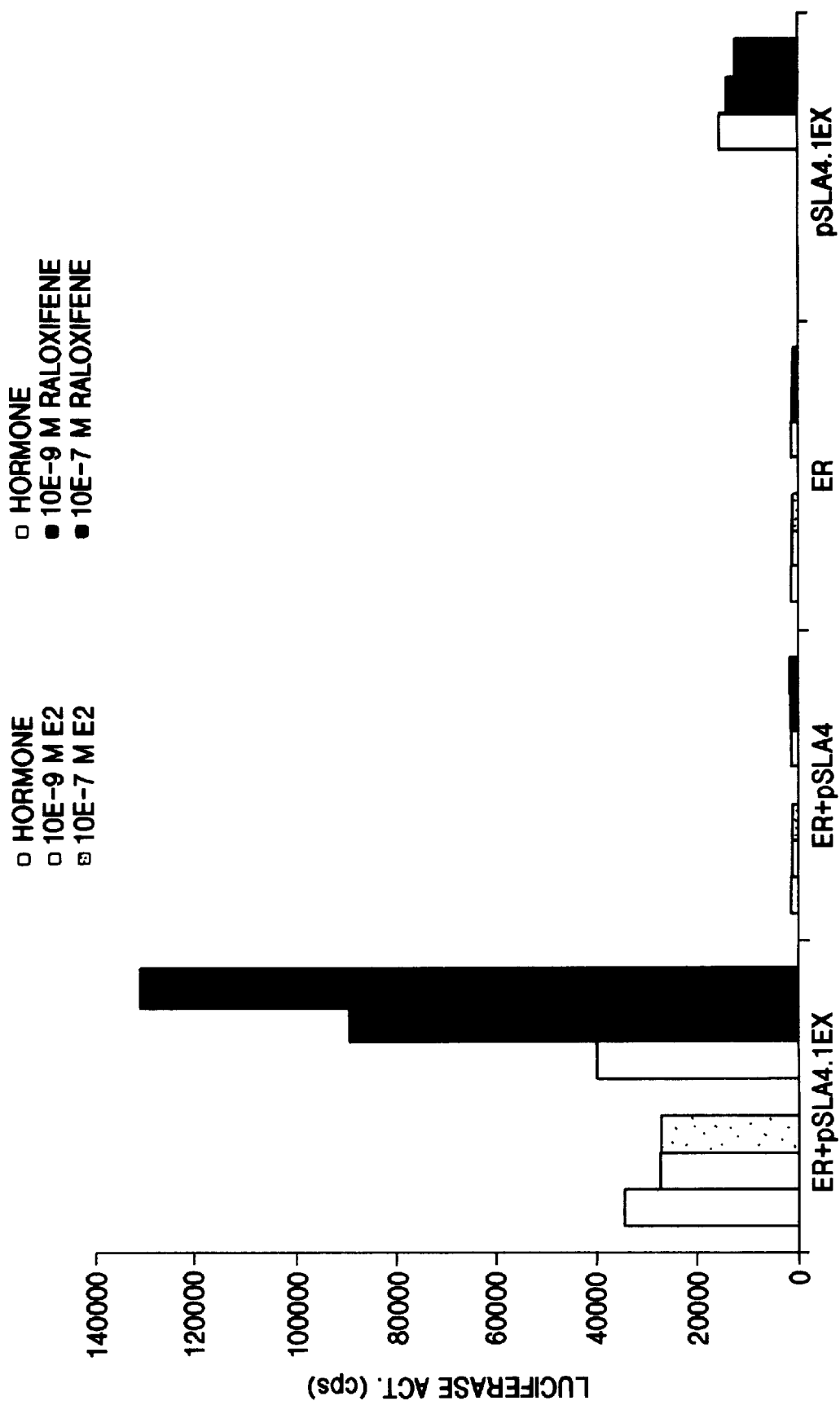
FIG. 7 Histogram showing the ER-mediated effect of raloxifene being dependent on the BMP-4 promoter 1 region as present in pSLA4.1EX and absent in pSLA4 reporter.

Moreover, the ER-mediated raloxifene effect as depicted in this figure, is based on the presence of the BMP-4 promoter 1 region of pSLA4.1EX (FIG. 7).

Figure 8A:
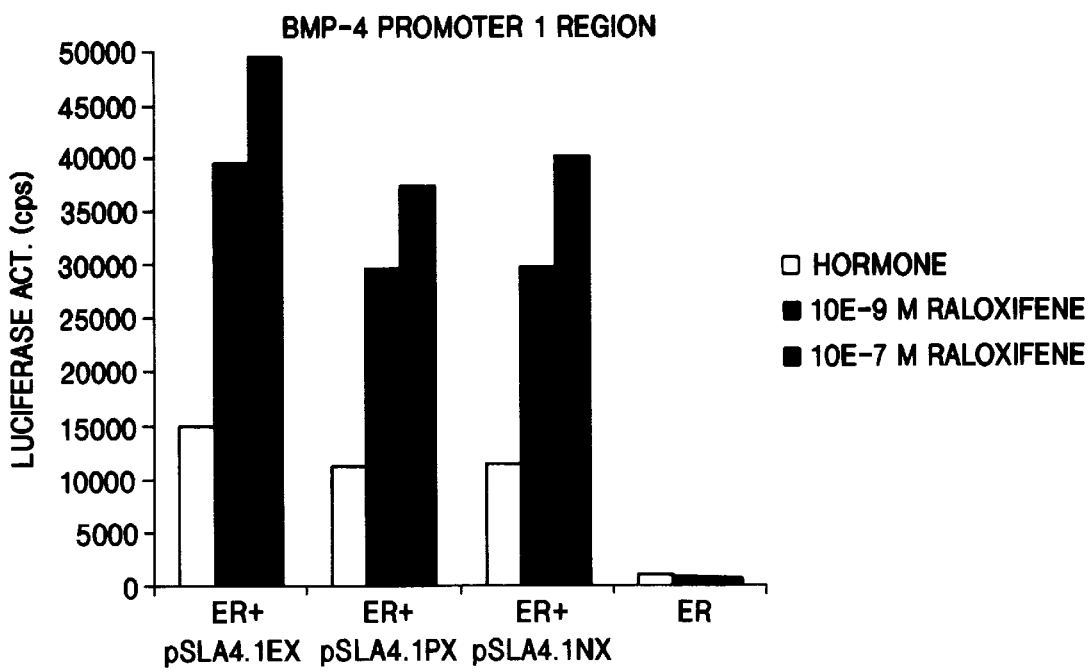
FIG. 8 Histogram showing the ER-mediated effect of raloxifene being present in both individual BMP-4 promoter region-containing reporters.
Figure 8B:
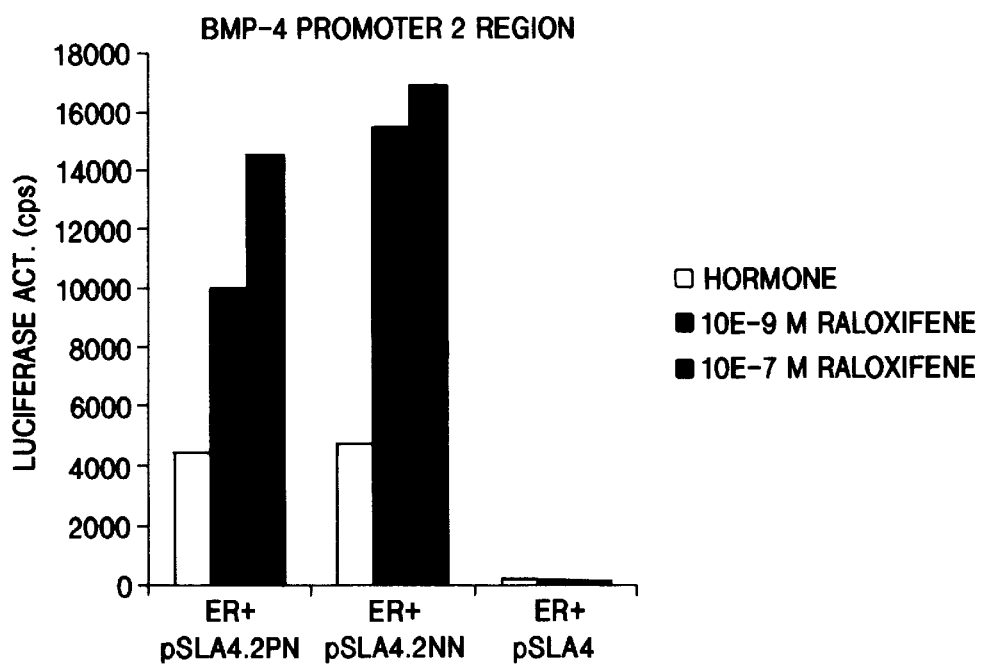

In addition, the ER-mediated raloxifene effect is not solely a characteristic of the BMP-4 promoter region 1, but was also apparent if the BMP-4 promoter 2 region was evaluated in a similar way (FIG. 8).

Generating different BMP-4 promoter region 1 constructs, it is demonstrated that although the intrinsic promoter activity is reduced, the ER-mediated raloxifene effect is not altered. Table 1 lists the various BMP-4 promoter 1 region constructs and their behavior in terms of a) promoter activity expressed as % of luciferase activity in the absence of hormone, taking pSLA4.1EX as 100%, and b) fold induction by estradiol and raloxifene calculated as the ratio of luciferase activity in the presence and absence of the indicated compound.

Figure 9:
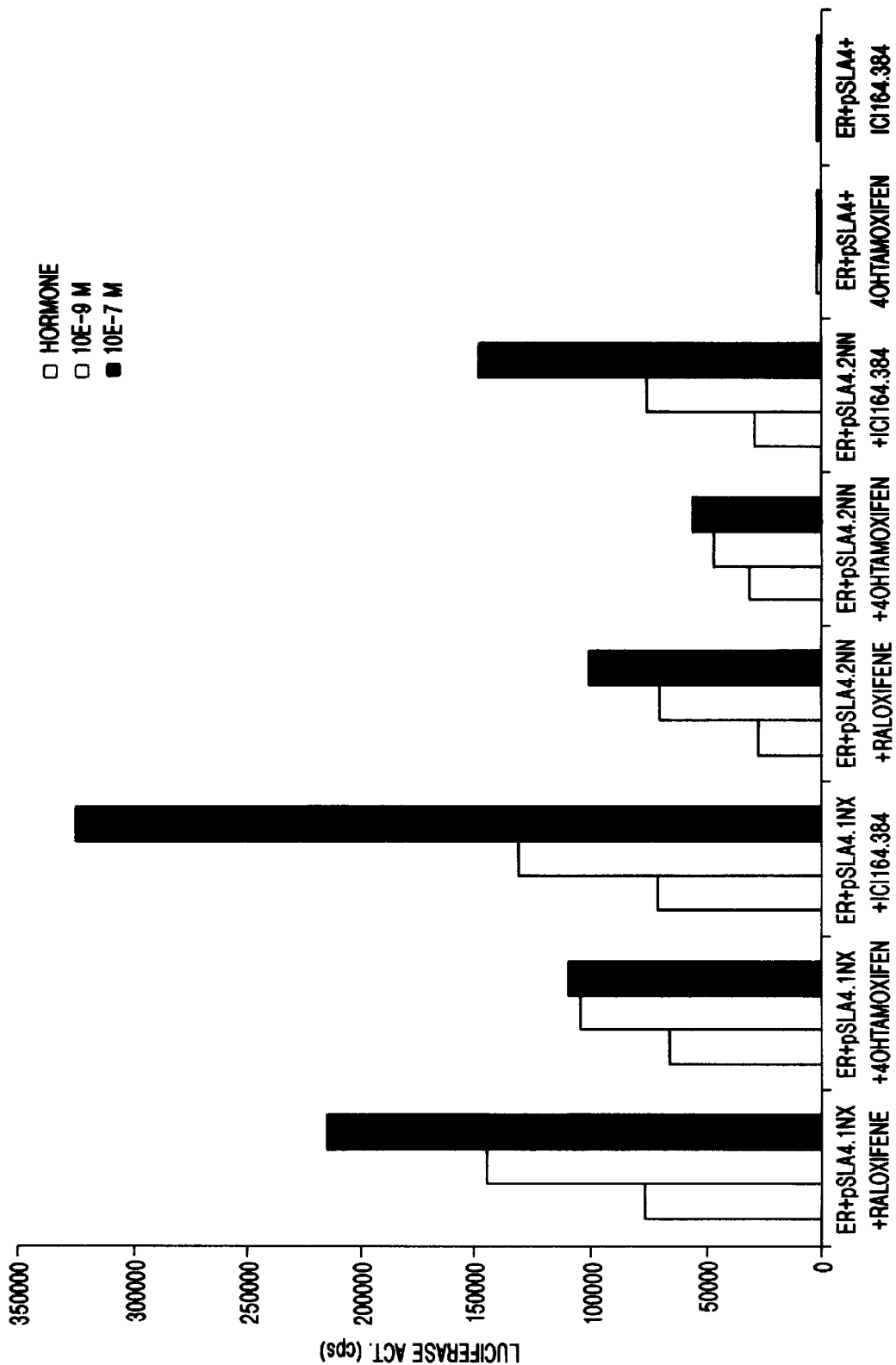
FIG. 9 Histogram showing the ER-mediated effects of raloxifene, 4-OH-tamoxifen and ICI 164.384 on both BMP-4 promoter region-containing reporters.

Finally, if analyzed for other therapeutic agents, the raloxifene effects shown above, can also be achieved by the compounds 4OH-tamoxifen and ICI 164384 (FIG. 9).

TABLE 1

| BMP-4 promoter 1 constructs | | Promoter Activity (%) | Fold Induction | |
|---|---|---|---|---|
| | | | Estradiol | Raloxifene |
| pSLA4.1EX |  EcoRI — XhoI — LUC | 100 | 0.7 ± 0.2 | 3.7 ± 0.7 |
| pSLA4.1PX | 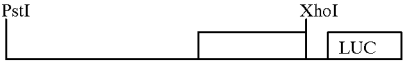 PstI — XhoI — LUC | 74 | 0.7 ± 0.2 | 3.3 ± 0.5 |
| pSLA4.INX | 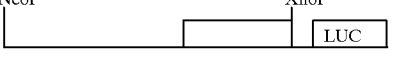 NcoI — XhoI — LUC | 74 | 0.7 ± 0.2 | 3.4 ± 0.5 |
| pSLA4.IN+33 | 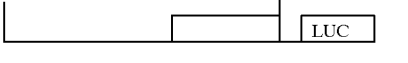 NcoI — +33 — LUC | 25 | 0.7 ± 0.2 | 3.1 ± 0.3 |
| pSLA4.IN+16 | 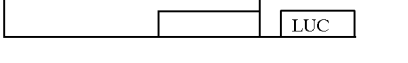 NcoI — +16 — LUC | 20 | 0.7 ± 0.1 | 3.8 ± 0.6 |

TABLE 1-continued

| BMP-4 promoter 1 constructs | | Promoter Activity (%) | Fold Induction | |
|---|---|---|---|---|
| | | | Estradiol | Raloxifene |
| pSLA4.IN–42 | NcoI ——— -42 ——[LUC]— | 10 | 0.7 ± 0.1 | 1.1 ± 0.2 |
| pSLA4 | [LUC] | 1 | 0.7 ± 0.1 | 1.1 ± 0.2 |
| pERE$_3$TATA-Luc | (ERE$_3$) TATA [LUC] | 100 | 26 ± 7 | 0.7 ± 0.3 |

What is claimed is:

1. An isolated human BMP-4 promoter region, or a fragment thereof that modulates and/or controls the expression of the downstream encoding sequences of a gene, wherein said promoter region has the nucleic acid sequence of SEQ ID NO: 1 or SEQ ID NO: 2.

2. A vector comprising the BMP-4 promoter region or fragment according to claim 1, wherein the promoter region or fragment is operably linked to a gene.

3. A host cell comprising the BMP-4 promoter region or fragment thereof according to claim 1.

4. A method for the identification of a potential therapeutic agent for the prevention and/or treatment of osteoporosis, comprising:

(a) introducing into a cell a first expression vector comprising the isolated human BMP-4 promoter region or fragment thereof according to claim 1 operably linked to a reporter gene, and a second expression vector comprising DNA encoding an estrogen receptor;

(b) contacting said cell with a candidate agent; and (c) monitoring the expression of the protein encoded by the reporter gene, wherein induced expression of the protein indicates that the candidate agent is a potential therapeutic agent.

5. A vector comprising an isolated human BMP-4 promoter region having the nucleic acid sequence of SEQ ID NO:1 SEQ ID NO:2.

6. The vector of claim 2, wherein said gene is a reporter gene.

7. A host cell comprising the vector according to claim 2.

8. A host cell comprising the vector according to claim 5 or claim 6.

* * * * *

SEQUENCE LISTING

<160> NUMBER OF SEQ ID NOS: 16

<210> SEQ ID NO 1
<211> LENGTH: 1456
<212> TYPE: DNA
<213> ORGANISM: human

<400> SEQUENCE: 1

```
gaattccgga tctgggcaag tccctttaac ctggtagtcc ttcctttcct tgtttgtaaa      60
acagagagat gaggctgata gctccctcac agctccatca gaggcagtgt gtgaaattag     120
ttcctgtttg ggaaggttta aaagccacca cattccacct ccctgctaat atgattacta     180
aaatgttttt atatgaaagg gccaattcct catctcccct cttcctttaa aaacagacca     240
agggcatct tttcttgtct ccctgtggcc taaaggttta ctgcttctgt ggttatctcc      300
ttggaaagac agagtgtcag gactcttagg tacaccaaaa atgaacaaaa aaatcaacaa     360
caaccataac accaacaaaa ataactgctg tgtcggttct taagacggct tctgagctag     420
aaacagattt ttctaactgt aaaaaacgtg gccccagcct gtctgcaggc cacctctgtc     480
tttaggcctt ggggggagga gggaagtgag ctcatttact ggggtctacc tcagggtcat     540
caccaaggtg ttctacaaaa cgcactttaa gaatgttttg gaaggaaatt caccttttaa     600
cagcccaaga ggtatctctc tctggcacac agttctgcac acagcctgtt tctcaacgtt     660
tggaaatctt ttaacagttt atggaaggcc accttttaaa ccgatccaac agctcctttc     720
tccataacct gattttagag gtgtttcatt atctctaatt actcagggta aatggtgatt     780
actcagtgtt ttaatcatca gtttgggcag cagttacact aaactcaggg aagcccagac     840
tcccatgggt atttttggaa ggtacggcga ctagtcggtg catgctttct agtacctccg     900
cacgtggtcc ccaggtgagc cccagccgct cccagagct ggaggcagcg gcgtcccagc      960
tccgacggca gctgcggact cgggcgctgc ctgggtattc cgggaccagg gcctgctagg    1020
cgaggtcggg cggctggagg gaggatgtgg gcgggctccc atccccagaa agggaggcga    1080
gcgagggagg agggaaggag ggaggggccg ccggggaaga ggaggaggaa ggaaagaaag    1140
aaagcgaggg agggaaagag gaggaaggaa gatgcgagaa ggcagaggag gagggaggga    1200
gggaaggagc gcggagcccg gcccggaagc taggtgagtg tggcatccga gctgagggac    1260
gcgagcctga gacgccgctg ctgctccggc tgagtatcta gcttgtctcc cgatgggatt    1320
cccgtccaag ctatctcgag cctgcagcgc cacagtcccc ggcctcgcc caggttcact     1380
gcaaccgttc agaggtcccc aggagctgct gctggcgagc ccgctactgc agggacctat    1440
```

```
                                           -continued ggtgagcaag gctacc                                                    1456

<210> SEQ ID NO 2
<211> LENGTH: 1377
<212> TYPE: DNA
<213> ORGANISM: human

<400> SEQUENCE: 2
ggcttcttcc agcgggagtt ggtccggggg ccttagaggc tccaagcact gctttggagg      60
atggtttcca aggatcgcgg tttgtgagtt gaaggccttt gtgagaggtt aaaccccaa     120 aagatacata cttggtaaac tgaggctacc tgtaaacaca tttcggcatt aggagaagat    180
tcgagtaggg aagtgaagga caaccacccg aggttacatt cctttccccc aataaaaagc    240
tctggggatg aaagttcttt tggcttttat cttttcgatt taaaaatttg agaagaaaaa    300
tgtgactaga gatgaatcct ggtgaatccg aaattgaaac acaactcccc cttcccttc     360 ctatcctctc ggttttagaa ccgcgctctc ccgcccagg agattccttg gggccgaggg     420
ttttccgggg aacccgggcg ctcgccctt ctactgtccc tttgccccgc gggcacagct     480
tgcctccgtc tgctttctct acttctggac ctctcctcgc cgggcttatt aaagggcttc    540
tgcgtctcaa aacaaaacaa aaaaacccct tgctcttccc aacccttcg cagcccgccc     600 cagcggtggc gcgggaccag caaaggcgaa agccgcgcgg ctcttgaccg ggcgcggacg    660
gtcgcgcagg gcgcccgcgg cctccgcacc cggacctgag gtgttggtcg actccgggca    720
tccacggtcg ggagggaggg ctgagctgtt cgatccttta cttttcttcc tcaaagtcta    780
cctgccaatg cccctaacaa caaaaccaag tatgtgcgtg gagagtgggg cggcaggcaa    840
cccgagttct tgagctccgg agcgacccaa agcagcaact gggaacagcc tcaggaaagg    900
gaggtcgggt ggagtgggct ttggggcagg agtcatgggg cccggggcgg acgacctggc    960
cctcccggcc ctgctgaacg ctgagttgcg cctagtcggg ttttcgaaga ggcccttgcc   1020
cagagcaccc acgcgcgcgg cacgatcttc gattagtcag acatcccag taactgcttg    1080 aactgtaggt aggtaaaatt cttgaaggag tatttgctgc gtgcgactct gctgctggtg   1140
caacggagga agggggtgg ggaaggaagt ggcgggggaa gagtgtggtg gtggtttaaa    1200
aaataaggga agccgaggcg agagagacgc agacgcagag gtcgagcgca ggccgaaagc   1260
tgttcaccgt tttctcgact ccgggaacat ggtgggattt cctttctgcg ccgggtcggg   1320
agttgtaaaa cctcggccac attaagatct gaaaactgtg atgcgtcctt tctgcag     1377

<210> SEQ ID NO 3
<211> LENGTH: 30
<212> TYPE: DNA
<213> ORGANISM: Artificial Sequence
<220> FEATURE:
<221> NAME/KEY: primer_bind
<222> LOCATION: (1)..(30)
<220> FEATURE:
<223> OTHER INFORMATION: Description of Artificial Sequence: primer

<400> SEQUENCE: 3
cgcggatccc aagtttgttc aagattggct                                       30

<210> SEQ ID NO 4
<211> LENGTH: 29
<212> TYPE: DNA
<213> ORGANISM: Artificial Sequence
<220> FEATURE:
<221> NAME/KEY: primer_bind
```

```
<222> LOCATION: (1)..(29)
<220> FEATURE:
<223> OTHER INFORMATION: Description of Artificial Sequence: primer

<400> SEQUENCE: 4
cgcggatccg cctgatctca gcggcaccc                                    29

<210> SEQ ID NO 5
<211> LENGTH: 24
<212> TYPE: DNA
<213> ORGANISM: Artificial Sequence
<220> FEATURE:
<221> NAME/KEY: primer_bind
<222> LOCATION: (1)..(24)
<220> FEATURE:
<223> OTHER INFORMATION: Description of Artificial Sequence: primer

<400> SEQUENCE: 5
gcattcggtt accaggaatc atgg                                         24

<210> SEQ ID NO 6
<211> LENGTH: 21
<212> TYPE: DNA
<213> ORGANISM: Artificial Sequence
<220> FEATURE:
<221> NAME/KEY: primer_bind
<222> LOCATION: (1)..(21)
<220> FEATURE:
<223> OTHER INFORMATION: Description of Artificial Sequence: primer

<400> SEQUENCE: 6
cagctcggat gccacactca c                                            21

<210> SEQ ID NO 7
<211> LENGTH: 18
<212> TYPE: DNA
<213> ORGANISM: Artificial Sequence
<220> FEATURE:
<221> NAME/KEY: primer_bind
<222> LOCATION: (1)..(18)
<220> FEATURE:
<223> OTHER INFORMATION: Description of Artificial Sequence: primer

<400> SEQUENCE: 7
catgttcccg gagtcgag                                                18

<210> SEQ ID NO 8
<211> LENGTH: 11
<212> TYPE: DNA
<213> ORGANISM: human
<220> FEATURE:
<221> NAME/KEY: TATA_signal
<222> LOCATION: (1)..(11)

<400> SEQUENCE: 8
gggtatataa t                                                       11

<210> SEQ ID NO 9
<211> LENGTH: 15
<212> TYPE: DNA
<213> ORGANISM: human
<220> FEATURE:
<221> NAME/KEY: misc_signal
<222> LOCATION: (1)..(15)
<223> OTHER INFORMATION: estrogen response element

<400> SEQUENCE: 9
aggtcacagt gacct                                                   15
```

```
<210> SEQ ID NO 10
<211> LENGTH: 21
<212> TYPE: DNA
<213> ORGANISM: human
<220> FEATURE:
<221> NAME/KEY: misc_feature
<222> LOCATION: (1)..(21)
<223> OTHER INFORMATION: splice site 3'terminus exon 1

<400> SEQUENCE: 10
cctatggtga gcaaggctac c                                              21

<210> SEQ ID NO 11
<211> LENGTH: 21
<212> TYPE: DNA
<213> ORGANISM: human
<220> FEATURE:
<221> NAME/KEY: misc_feature
<222> LOCATION: (1)..(21)
<223> OTHER INFORMATION: splice site 3'terminus exon 2

<400> SEQUENCE: 11
aacatggtgg gatttccttt c                                              21

<210> SEQ ID NO 12
<211> LENGTH: 21
<212> TYPE: DNA
<213> ORGANISM: human
<220> FEATURE:
<221> NAME/KEY: misc_feature
<222> LOCATION: (1)..(21)
<223> OTHER INFORMATION: splice site 5'terminus exon 2

<400> SEQUENCE: 12
aaatattcct tttaggagcc a                                              21

<210> SEQ ID NO 13
<211> LENGTH: 21
<212> TYPE: DNA
<213> ORGANISM: human
<220> FEATURE:
<221> NAME/KEY: misc_feature
<222> LOCATION: (1)..(21)
<223> OTHER INFORMATION: splice site 3'terminus exon 3

<400> SEQUENCE: 13
ctgtcagtca gtagacacct g                                              21

<210> SEQ ID NO 14
<211> LENGTH: 21
<212> TYPE: DNA
<213> ORGANISM: human
<220> FEATURE:
<221> NAME/KEY: misc_feature
<222> LOCATION: (1)..(21)
<223> OTHER INFORMATION: splice site 5'terminus exon 3

<400> SEQUENCE: 14
cttccccctc cccagagaca c                                              21

<210> SEQ ID NO 15
<211> LENGTH: 21
<212> TYPE: DNA
<213> ORGANISM: human
<220> FEATURE:
<221> NAME/KEY: misc_feature
<222> LOCATION: (1)..(21)
```

```
<223> OTHER INFORMATION: splice site 3'terminus exon 4

<400> SEQUENCE: 15
acgaaggtca gtctcattac c                                              21

<210> SEQ ID NO 16
<211> LENGTH: 21
<212> TYPE: DNA
<213> ORGANISM: human
<220> FEATURE:
<221> NAME/KEY: misc_feature
<222> LOCATION: (1)..(21)
<223> OTHER INFORMATION: splice site 5'terminus exon 4

<400> SEQUENCE: 16
cctaactgtg cctagaacat c                                              21
```